(12) United States Patent
Walser et al.

(10) Patent No.: US 10,765,713 B2
(45) Date of Patent: Sep. 8, 2020

(54) CANNABIS COMPOSITIONS AND METHODS

(71) Applicant: 3277991 NOVA SCOTIA LIMITED, Truro, Nova Scotia (CA)

(72) Inventors: Lennie Walser, Bible Hill (CA); David Morgan, Antigonish Landing (CA); Marcel Gignac, Amherst (CA); Evan Price, Truro (CA)

(73) Assignees: 3277991 NOVA SCOTIA LIMITED, Truro, Nova Scotia (CA); KANNABLISS TECHNOLOGIES INC., Amherst, Nova Scotia (CA)

( * ) Notice: Subject to any disclaimer, the term of this patent is extended or adjusted under 35 U.S.C. 154(b) by 66 days.

(21) Appl. No.: 16/311,194

(22) PCT Filed: Jun. 30, 2017

(86) PCT No.: PCT/CA2017/050800
§ 371 (c)(1),
(2) Date: Dec. 19, 2018

(87) PCT Pub. No.: WO2018/006165
PCT Pub. Date: Jan. 11, 2018

(65) Prior Publication Data
US 2019/0321425 A1  Oct. 24, 2019

Related U.S. Application Data

(60) Provisional application No. 62/357,999, filed on Jul. 3, 2016.

(51) Int. Cl.
| | | |
|---|---|---|
| *A61K 36/00* | (2006.01) |
| *A61K 36/185* | (2006.01) |
| *A61P 23/00* | (2006.01) |
| *A61K 31/05* | (2006.01) |
| *A61K 31/352* | (2006.01) |
| *A61K 47/44* | (2017.01) |

(52) U.S. Cl.
CPC ............ *A61K 36/185* (2013.01); *A61K 31/05* (2013.01); *A61K 31/352* (2013.01); *A61K 47/44* (2013.01); *A61P 23/00* (2018.01)

(58) Field of Classification Search
CPC ....................................................... A61K 36/00
USPC ....................................................... 424/725
See application file for complete search history.

(56) References Cited

U.S. PATENT DOCUMENTS

| | | |
|---|---|---|
| 7,344,736 B2 | 3/2008 | Whittle et al. |
| 9,186,386 B2 | 11/2015 | Speier |
| 2011/0256245 A1 | 10/2011 | Rosenblatt et al. |

FOREIGN PATENT DOCUMENTS

| | | |
|---|---|---|
| WO | 2010/150245 | 12/2010 |
| WO | 2016/064987 | 4/2016 |

OTHER PUBLICATIONS

Lakhan et al, "Whole plant cannabis extracts in the treatment of spasticity in multiple sclerosis: a systematic review" BMC Neurology, 9:59 6 pages (2009).
Barnes "Sativex: clinical efficacy and tolerability in the treatment of symptoms of multiple sclerosis and neuropathic pain" Expert Opinion Pharmacother., 7(5):607-615 2006.
McPartland et al. "Cannabis and cannabis extracts: greater than the sum of their parts?" Journal of Cannabis Therapeutics, 1(3-4):103-132 2001.
Extended European Search Report corresponding to European Patent Application No. 17823369.8, dated Feb. 14, 2020, 11 pages.
International Search Report and Written Opinion, PCT/CA2017/050800, dated Oct. 16, 2017, 11 pages.
International Preliminary Report on Patentability corresponding to International Application No. PCT/CA2017/050800, dated Jan. 17, 2019, 8 pages.

*Primary Examiner* — Michael V Meller
(74) *Attorney, Agent, or Firm* — Myers Bigel, P.A.

(57) ABSTRACT

A composition comprises an extract from a first cannabis plant tissue and an extract from a second cannabis plant tissue.

4 Claims, 13 Drawing Sheets

CANNABIS COMPOSITIONS AND METHODS

STATEMENT OF PRIORITY

This application is a 35 U.S.C. § 371 national phase entry of International Application No. PCT/CA2017/050800, filed Jun. 30, 2017, which claims the benefit, under 35 U.S.C. § 119(a) of U.S. Provisional Application No. 62/357,999, filed Jul. 3, 2016, the entire contents of each of which are incorporated herein by reference herein.

FIELD

The present invention relates to cannabis compositions and methods. More specifically, the present invention is, in aspects, concerned with compositions that approximate a whole-plant cannabis extract as well as related methods of making and using the compositions.

BACKGROUND

Cannabis compositions are traditionally administered via inhalation. Although this is a fast delivery method, it is difficult to control the exact amounts of cannabinoids that are being delivered, as some are lost or converted to other compounds when burned and different people absorb different amounts of cannabinoids through their lung tissue due to their individual biochemical differences as well as their idiosyncratic smoking habits.

In other cases, cannabis compositions are administered in edible compositions. However, the concerns identified above with regard to control of dosing also apply to edible compositions, especially as the typical extraction methods used in preparing cannabis for cooking involve heat. Additionally, each individual's recipe(s) are idiosyncratic, just as smoking are.

Furthermore, cannabis compositions are typically derived exclusively from the dried, unfertilized, female flowers of the plant. However, cannabinoids and other active ingredients, such as the great variety of terpenes which may be present in the plant also occur on, and in, the leafy parts of the plant, especially those which are found near the unfertilized female flowers, on to which the glandular secretions of the flowers will have fallen during growth, harvesting, and processing. Additionally, hemp seed oil, which may be pressed from the seeds of the plant, is a well-known, commercially available health food, but is rarely, if ever encountered as part of a cannabis composition.

There is a need for alternative therapies to overcome or mitigate at least some of the deficiencies of the prior art.

SUMMARY

In accordance with an aspect, there is provided a composition comprising an extract from a first cannabis plant tissue and an extract from a second cannabis plant tissue.

In an aspect, the first and second cannabis plant tissues are of the same species.

In an aspect, the first and second cannabis plant tissues are of the same strain.

In an aspect, the first and second cannabis plant tissues are of different strains.

In an aspect, the first and second cannabis plant tissues are of different species.

In an aspect, the first and second cannabis plant tissues are independently selected from fresh and dried.

In an aspect, the first and second cannabis plant tissues are independently selected from the group consisting of flowers, leaves, stems, roots, and seeds.

In an aspect, the first cannabis plant tissue is flower tissue.

In an aspect, the flower tissue is bud tissue.

In an aspect, the bud tissue is sinsemilla.

In an aspect, the second cannabis plant tissue is leaf tissue.

In an aspect, the leaf tissue is trim.

In an aspect, the composition further comprises an extract from a third cannabis plant tissue.

In an aspect, the third cannabis plant tissue is of the same species as at least one of the first and the second cannabis plant tissue.

In an aspect, the third cannabis plant tissue is of the same strain as at least one of the first and the second cannabis plant tissue.

In an aspect, the third cannabis plant tissue is of a different species than the first and second cannabis plant tissue.

In an aspect, the composition further comprises a diluent.

In an aspect, the diluent is an oil or butter or combination thereof.

In an aspect, the diluent is clarified butter.

In an aspect, the diluent is an oil.

In an aspect, the oil is plant-derived.

In an aspect, the oil is hemp seed oil or olive oil.

In an aspect, the composition further comprises at least one pharmaceutical agent.

In an aspect, the pharmaceutical agent is selected from the group consisting of a vitamin (such as vitamin D), an analgesic, a muscle relaxant, and an anti-inflammatory agent.

In an aspect, one or more of the extracts are prepared by an extraction method selected from the group consisting of Soxhlet extraction, solvent-extraction, solventless-extraction, super-critical fluid extraction, the application of pressure and/or heat, and combinations thereof.

In an aspect, the extraction method uses a polar or non-polar solvent.

In an aspect, the solvent is selected from the group consisting of an alcohol (such as isopropyl alcohol), an acid, a super- or sub-critical fluid under controlled combinations of temperature and pressure, and/or a combination thereof.

In an aspect, the composition further comprises at least one excipient.

In an aspect, the excipient is selected from the group consisting of thickeners, fillers, and tableting agents.

In an aspect, the excipient is selected from maltodextrin, microcrystalline cellulose, and combinations thereof.

In an aspect, the composition is formulated for enteral delivery.

In an aspect, the composition is formulated into a tablet or capsule.

In an aspect, the composition is formulated for parenteral delivery.

In an aspect, the composition is formulated for injection, inhalation, transdermal delivery, or sublingual delivery.

In an aspect, the extract from the first and second cannabis plant tissues interact synergistically to treat and/or prevent a disease and/or symptom of a disease.

In an aspect, the composition approximates a whole-plant extract.

In accordance with an aspect, there is provided a method of treating and/or preventing a disease and/or symptom of a disease, the method comprising administering the composition described herein.

In accordance with an aspect, there is provided a drug delivery form that provides cannabis-derived active agents in a reproducible dose.

In accordance with an aspect, there is provided a drug delivery form that is simple for physicians to dose and titrate to a subject's needs.

In accordance with an aspect, there is provided a drug delivery form that provides cannabis-derived active agents that are relatively more stable than those agents in a smokable or traditionally ingestible form.

In accordance with an aspect, there is provided a method of tailoring a treatment regime for an individual subject, the method comprising administering the described herein.

In accordance with an aspect, there is provided a method of reducing the use of smoked cannabis in a subject, the method comprising administering the composition described herein.

Other features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
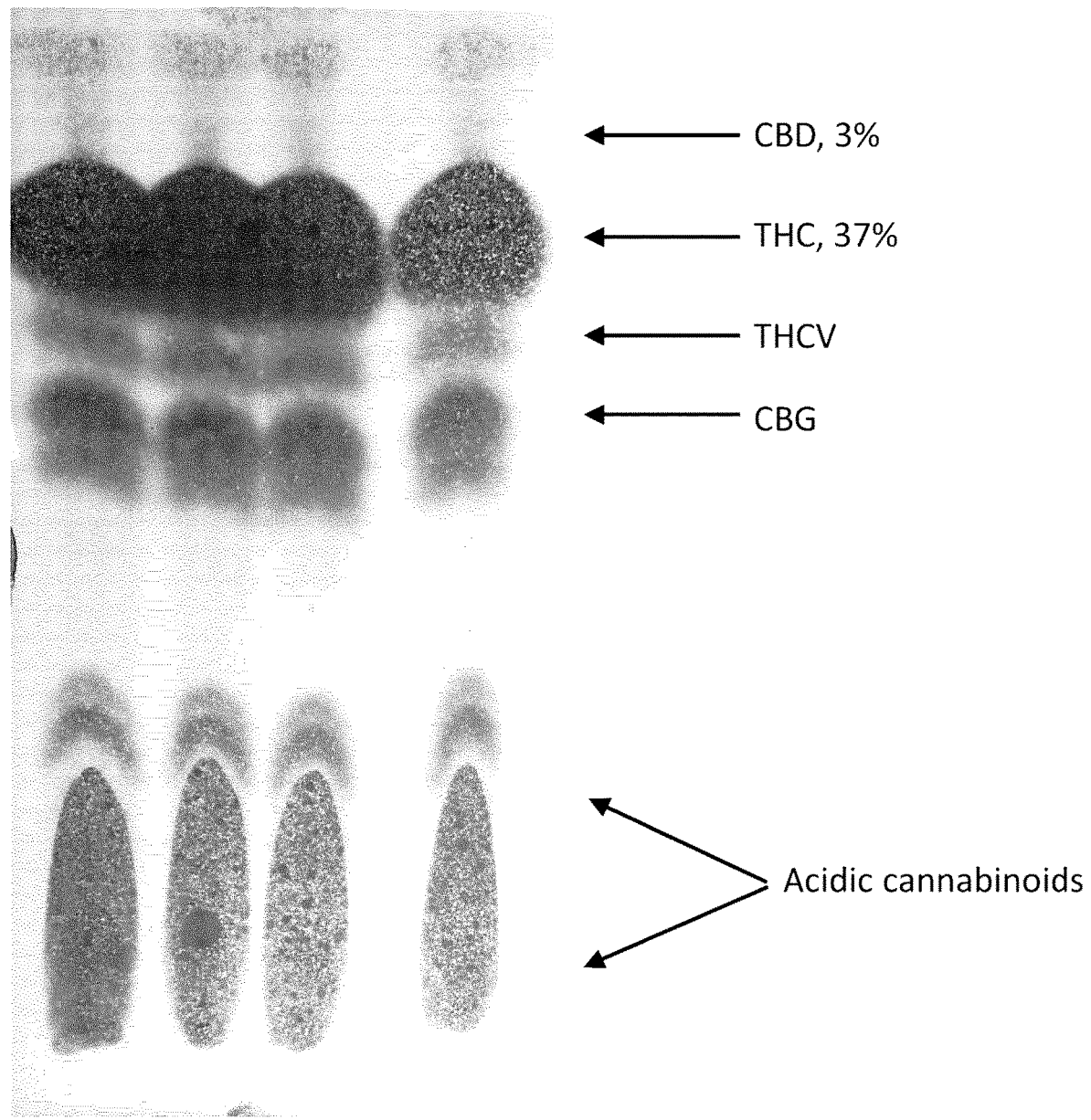
FIG. 1 shows a representative cannabinoid analysis of whole plant extract by Cannalytics® "Cannabis Analysis Test" kit, in which THC was observed to be present at 37% by weight and CBD was observed to be present at 3% by weight.

Medical cannabis is typically provided in the form of the dried, unfertilized, female flowers prepared so that it is suitable for smoking. Anecdotal evidence from the community of medical cannabis users, the community of recreational cannabis users, and, increasingly, sound scientific evidence provided by the academic and professional medical communities, has strongly suggested that different strains of cannabis produce different medically relevant effects. For reviews, see Russo, Ethan, and Geoffrey W. Guy. 2006. "A Tale of Two Cannabinoids: The Therapeutic Rationale for Combining Tetrahydrocannabinol and Cannabidiol." Medical Hypotheses 66 (2): 234-46; Russo, Ethan B. 2011. "Taming THC: Potential Cannabis Synergy and Phytocannabinoid-Terpenoid Entourage Effects." British Journal of Pharmacology 163 (7): 1344-64. Each of these references is incorporated by reference in its entirety.

Furthermore, the effects of cannabis preparations are not limited to the cannabinoids present, as terpene contents can also be relevant. Therefore, as will be described herein, there is a great, and presently untapped, potential of whole-plant extracts of cannabis plants formulated in such a way as to provide a standardized dose of medically relevant ingredient. Such whole-plant extracts may be derived from individual strains or multiple strains of cannabis, or from one or more tissues of a given strain, or multiple strains.

Described herein are compositions that approximate a whole-plant cannabis extract for administration to patients via many different routes. In typical aspects, at least two extracts from different parts of one or more cannabis plants are obtained, such as from the leaves or trim and the flowers. These extracts are combined together and typically diluted with an oil, such as hemp seed oil. The composition may be administered as-is, or it may be further formulated into, for example, a tablet, capsule, a lozenge, a mint, a chewing gum, an edible food or beverage product, a suppository, or a pessary, or modified for administration parenterally, such as via inhalation.

Definitions

The term "cannabis" refers to any member of the genus *Cannabis*, including *Cannabis sativa*, *Cannabis indica*, and *Cannabis ruderalis*, as well as any strains or hybrids thereof. The term "cannabis" also includes whole cannabis plants as well as portions and tissues of cannabis plants.

The term "sinsemilla" refers to the unfertilized flowers of female cannabis plants, which do not produce seeds. Sinsemilla produce glandular secretions that tend to be enriched in cannabinoids and terpenes.

The term "trichome" refers to fine glandular outgrowths on sinsemilla that secrete cannabinoids and terpenes. Trichomes are fragile, and may fall onto nearby leafy material during routine operations like harvesting and trimming. Thus, "trim," defined below, tends to be enriched in trichomes.

The term "trim" refers to the leafy parts of a cannabis plant, particularly those found near sinsemilla, which therefore also tend to be covered in trichomes.

The term "cannabinoid" refers to any one or more of the over 100 known members of the phytocannabinoid family, including, for example, Δ9-tetrahydrocannabinol (THC), Δ9-tetrahydrocannabivarin (THCV), cannabidiol (CBD), cannabinol, cannabigerol, and cannabichromene.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder, or may render the subject more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat the symptoms of a specific disease or condition, such as, for example, arthritis, sleep conditions, spasticity, restless leg syndrome, stiffness, post-traumatic stress disorder, Alzheimer's disease, schizophrenia, depression, alcoholism, Parkinson's disease, stroke, premature labor, endotoxic shock, hepatic cirrhosis, atherosclerosis, cancer, bone implantation, glaucoma, emesis, pain, multiple sclerosis, amyotrophic lateral sclerosis, encephalitis, Huntington's disease, obesity, feeding, fasting, stress, memory, aging, hypertension, cirrhosis, septic shock, cardiogenic shock, cerebral ischemia, myocardial infarction, neurotoxicity, febrile seizures, various intestinal disorders, nausea and vomiting associated with cancer chemotherapy, and/or AIDS-related cachexia. Effective amounts of the compounds described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question, such as multiple sclerosis.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Cannabis Extracts

It will be understood that extracts of any portions or tissues of cannabis plants are included herein. Such portions or tissues include the flowers, leaves, stems, roots, and seeds. More typically, extracts are taken from flowers (e.g., sinsemilla) and leaves (e.g., trim) and combined together to approximate a whole-plant cannabis extract. Different tissues of cannabis plants contain different profiles of cannabinoids, terpenes, and other active agents and, therefore, approximating a whole-plant extract may provide advantageous combinations of components. The tissues used for extraction may be fresh, meaning they have not been dried and/or cured, or they may be dried and/or cured tissues. Combinations of fresh and dried tissues are contemplated for use herein.

The extracts may be obtained through any known extraction method. In aspects, the extraction method may be Soxhlet extraction, solvent-extraction, solventless-extraction, super-critical fluid extraction, the application of pressure and/or heat, or combinations thereof. Different extraction methods may be used to obtain different extract profiles and/or purity levels, as would be understood by a skilled person.

In typical aspects, the extracts are prepared through a solvent extraction method. Briefly, the plant tissues are provided whole, torn, crushed, cut, shredded, milled, pulverized, or otherwise mechanically treated and are mixed with a solvent in any desired ratio. Typically about 1-10 parts cannabis are mixed with 1-10 parts solvent. In a typical aspect, about 1 part by weight of cannabis is mixed with about 8 parts by volume of solvent.

The solvent may be any desired aqueous or non-aqueous liquid, chosen based upon the cannabis plant tissue being extracted and the desired end-profile of the extract. For example, the solvent may be selected from the group consisting of methanol, ethanol, isopropanol, acetone, acetonitrile, butane, pentane, hexane, cyclohexane, super- or sub-critical carbon dioxide, chloroform, carbon tetrachloride, tetrahydrofuran, turpentine, benzene, toluene, and other organic solvents known to persons skilled in the art, water (which may or may not contain mineral or organic acids, inorganic or organic bases, buffering agents, lipids such as lecithin, fatty acids, and fatty alcohols, or combinations thereof), butter, clarified butter, hemp seed oil, olive oil, or other plant or animal derived oils, fats, or waxes, or combinations thereof.

The extractions may be carried out using conventional equipment, as would be understood by a skilled person. For example, the extractions may be carried out on a benchtop in an open or closed container, a beaker, a flask, a pot, a bowl, a bottle, a blender, a separatory funnel, an apparatus designed to create, deliver, or manipulate super- and/or sub-critical carbon dioxide or other super- or sub-critical fluid, using distillation equipment, or using Soxhlet or other extraction equipment.

The extractions may be carried out with or without agitation, stirring, shaking, or combinations thereof. Time periods for extraction may range from about 30 seconds up to an unlimited time. Reduced or elevated temperatures and/or pressures may be used. Once the extraction is complete, the liquid and solid phases are separated by any known method, such as decanting, centrifugation, rotary evaporation, benchtop evaporation via the application of heat, evaporation under a stream of inert gas, evaporation under reduced pressure, filtration, including the use of more than one filtration step, and/or more than one size of filtration membrane, and/or combinations of two or more of any of these means.

The solid phase may or may not be washed. Washes may be accomplished with the same or a different solvent from that which was used for the extraction step. The wash may be mixed with the liquid phase from the extraction.

Optionally, the resulting liquid phase may be extracted a second time, for example, by using different solvent, and/or a solvent immiscible with the first solvent. If so, subsequent phase separation may be carried out by the use of separatory funnels, centrifugation, aspiration, cannulation, or combinations thereof.

Optionally, resulting liquid may then be modified in many ways, including, for example, dilution, adjustment of pH, cooling, heating, mixing and subsequent separation from an immiscible co-solvent, or combinations thereof. If precipitation occurs, clarification may be accomplished through centrifugation, filtration, aspiration, or decanting. If phase separation occurs, phases may be separated by aspiration, centrifugation or the use of a separatory funnel, for example. Precipitated material, or material extracted into an immiscible co-solvent, may either be discarded, or used elsewhere in the process.

Solvent may be removed from the extract by any known method, such as decanting, centrifugation, rotary evaporation, benchtop evaporation at room temperature or via the application of heat, evaporation under a stream of inert gas, evaporation under reduced pressure, filtration, including the use of more than one filtration step, and/or more than one size of filtration membrane, and/or combinations of two or more of any of these means.

Compositions Comprising Cannabis Extracts

The cannabis extracts described herein, in aspects, are formulated into compositions. In typical aspects, the compositions comprise an extract from a first cannabis plant tissue, such as flower tissue, and an extract from a second cannabis plant tissue, such as leaf tissue. However, extracts from the same type of tissue from two or more different cannabis strains may be combined. Furthermore, more than two extracts may be combined, such as three, four, five, six, seven, eight, nine, ten or more extracts in various permutations, for example, trim and flowers from two or more different strains, trim from three different strains and flowers from two different strains, trim from one strain and flowers from two different strains, etc.

In aspects, the different extracts are combined in any ratio, such as from about 1:200 to about 200:1, such as from about 1:150, about 1:100, about 1:75, about 1:50, about 1:25, about 1:20, about 1:15, about 1:10, about 1:9, about 1:8, about 1:7, about 1:6, about 1:5, about 1:4, about 1:3, about 1:2, or about 1:1 to about 2:1, about 3:1, about 4:1, about 5:1, about 6:1, about 7:1, about 8:1, about 9:1, about 10:1, about 15:1, about 20:1, about 25:1, about 50:1, about 75:1, about 100:1, about 150:1, or about 200:1. In other aspects, the ratio of the two or more extracts is specifically selected to closely approximate the ratio found in the native plant. In yet other aspects, the ratio of the two or more extracts is specifically selected to provide the desired cannabinoid profile.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000), incorporated herein by reference in its entirety. On this basis, the compositions may include, albeit not exclusively, the cannabis extract(s) in association with one or more pharmaceutically acceptable vehicles or diluents, and may be contained in buffered solutions with a suitable pH that are iso-osmotic with physiological fluids.

In particular aspects, the extracts are combined together and diluted with an oil, fat, wax, or similar product, for example, lecithin. Some examples of vegetable oils suitable for diluting and/or dispersing the cannabis extract(s) include, but are not limited to coconut oil, olive oil, palm oil, palm kernel oil, sunflower seed oil, safflower oil, hemp seed oil, corn oil, macadamia seed oil, green coffee oil, kukui nut oil, jojoba seed oil, sweet almond oil, avocado oil, castor seed oil, sulfated castor oil, argan nut oil, acai berry oil, andiroba nut oil, apricot kernel oil, soybean oil, baobab seed oil, black raspberry seed oil, blackberry seed oil, blackcurrant fruit oil, blueberry seed oil, borage seed oil, broccoli seed oil, marula kernel oil, cucumber seed oil, manketti oil, passion flower seed oil, camelina seed oil, linseed seed oil, strawberry seed oil, poppy seed oil, moringa oil, rice bran oil, pomegranate oil, pumpkin seed oil, walnut seed oil, fish oil, fish liver oil, cod liver oil, shark liver oil, vegetable oil, canola oil, peanut oil, sesame oil, flaxseed oil, grape seed oil, almond oil, cottonseed oil, groundnut oil, teaseed oil, walnut oil, cashew oil, colza oil, hazelnut oil, marula oil, mongongo nut oil, pecan oil, perilla oil, pine nut oil, pistachio oil, rapeseed oil, watermelon seed oil, diacylglycerol oil, and any combination thereof.

Some examples of butters suitable for diluting and/or dispersing the cannabis extract(s) include, but are not limited to mango butter, aloe butter, olive butter, coffee bean butter, macadamia nut butter, avocado butter, cocoa butter, hemp butter, illipe butter, kokum butter, pistachio nut butter, shea butter, sweet almond butter, grape seed butter, mowrah butter, apricot butter, sal butter, soy butter, wheat germ butter, ghee, butter, clarified butter, and combinations thereof.

In typical aspects, the extracts are diluted with an oil of plant or animal origin, such as clarified butter, hemp seed oil, olive oil, or combinations thereof. In typical aspects, 1 ml of the extract is diluted with from 1-200 ml of the diluent, such as from about 1 ml to about 150 ml diluent, from about 1 to about 100 ml of the diluent, from about 1 ml to about 50 ml of the diluent, from about 1 ml to about 25 ml of the diluent, from about 1 ml to about 20 ml of the diluent, from about 1 ml to about 10 ml of the diluent, from about 50 ml to about 100 ml of the diluent, from about 25 ml to about 50 ml of the diluent, from about 10 ml to about 30 ml of the diluent, and any of the various ranges therein between. In typical aspects, about 1 ml of the extract is diluted with about 20 ml of the diluent.

In other aspects, the extracts are combined and then mixed with an excipient to produce a powder composition. For example, the extract and excipient can be mixed in any ratio to achieve a given drug strength and/or to achieve a desired physical form (such as liquid, wet powder, dry powder, etc.). Useful pharmaceutically acceptable excipients include but are not limited to: diluents such as microcrystalline cellulose (MCC), silicified microcrystalline cellulose ("SMCC", coprocessed 98% MCC and 2% colloidal silica and available from JRS Pharma of Rosenberg, Germany in various grades, e.g., Prosolv™ HD 90 having an average particle size of 110 μm and a density of 0.25-0.37 g/cm$^3$), microfine cellulose, lactose, starch, pregelatinized starch, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide and the like; binders such as acacia, guar gum, alginic acid, dextrin, maltodextrin, methylcellulose, ethyl cellulose, hydroxyethyl cellulose, hydroxypropyl cellulose (e.g. KLUCEL®), hydroxypropyl methylcellulose (e.g. METHOCEL®), carboxymethyl cellulose sodium, povidone (various grades of KOLLIDON®, PLASDONE®) starch and the like; disintegrants such as carboxymethyl cellulose sodium (e.g. Ac-Di-Sol®, Primellose®), crospovidone (e.g. Kollidon®, Polyplasdone®), povidone K-30, polacrilin potassium, starch, pregelatinized starch, sodium starch glycolate (e.g. Explotab®) and the like; surfactants including anionic surfactants such as chenodeoxycholic acid, 1-octanesulfonic acid sodium salt, sodium deoxycholate, glycodeoxycholic acid sodium salt, N-lauroylsarcosine sodium salt, lithium dodecyl sulfate, sodium cholate hydrate, sodium lauryl sulfate (SLS or SDS), cationic surfactants such as cetylpyridinium chloride monohydrate and hexadecyltrimethylammoniunn bromide, nonionic surfactants such as N-decanoyl-N-methylglucamine, octyl a-D-glucopyranoside, n-dodecyl b-D-maltoside (DDM), polyoxyethylene sorbitan esters like polysorbates and the like; plasticizers such as acetyltributyl citrate, phosphate esters, phthalate esters, amides, mineral oils, fatty acids and esters, glycerin, triacetin or sugars, fatty alcohols, polyethylene glycol, ethers of polyethylene glycol, fatty alcohols such as cetostearyl alcohol, cetyl alcohol, stearyl alcohol, oleyl alcohol, myristyl alcohol and the like. Solvents that are useful in layering or coating include but are not limited to: aqueous solvents such as water; organic volatile solvents such as acetaldehyde, acetone, benzene, carbon disulphide, carbon tetrachloride, 1,2 dichloroethane, dichloromethane, N,N-dimethylformamide, 1,4-dioxane, epichlorhydrin, ethyl acetate, ethanol, ethyl ether, ethylene glycol, 2-ethoxyethanol (acetate), formaldehyde, isopropanolol, methanol, methyl n-butyl ketone, methyl ethyl ketone, 2-methoxyethanol (acetate), perchloroethylene, toluene, 1,1,1-trichloroethane, trichloroethylene; and the like.

In typical aspects, the extracts are combined with maltodextrin (in any one or a variety of glucose equivalents, molecular weights, particle sizes, etc.) and/or microcrystalline cellulose (in any one or a variety of degrees of depolymerisation, particle size, etc.) to facilitate tableting and/or encapsulating the formulations.

Thus, pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the extracts, together with a suitable amount of carrier so as to provide the form for direct administration to the patient.

Pharmaceutical finished dosage forms of the extracts described herein may further include other ingredients, such as but not limited to pharmaceutically acceptable glidants, lubricants, opacifiers, colorants, and other commonly used excipients. The extracts described herein, or finished dosage forms, can further be optionally film coated, or enteric coated, or seal coated, or coated with substances to modify the release of the active ingredient(s). The coating can be done by any techniques such as powder coating, spray coating, dip coating, fluidized bed coating and the like. The release modifying and/or functional coating substances that can be used include but are not limited to: hydrophilic substances such as carboxymethyl cellulose sodium, hydroxyethyl cellulose, hydroxypropyl methylcellulose (HPMC); homopolymers or copolymers of N-vinylpyrrolidone; vinyl and acrylic polymers; polyacrylic acid and the like; hydrophobic substances such as celluloses like ethyl cellulose, low substituted hydroxypropyl cellulose (L-HPC), cellulose acetate, cellulose propionate (lower, medium or higher molecular weight), cellulose acetate propionate, cellulose acetate butyrate, cellulose acetate phthalate; polyalkyl methacrylates; polyalkyl acrylates; polyvinyl acetate (PVA); chitosan; crosslinked vinylpyrrolidone polymers; hydrogenated castor oil and the like. Other classes of rate controlling substances or their mixtures in various ratios as required are also within the purview of the dosage forms described herein without limitation.

Solvents used in the context of the extracts described herein in the processes of preparation of, or coating of tablets, capsules, etc. prepared from the extracts described herein, include but are not limited to water, isopropyl alcohol, dichloromethane, acetone, ethanol, ethyl acetate, or combinations thereof in any ratio suitable for processing the compositions. Components in the solvent or solvent mixture may be present in solution or dispersion form in any ratio suitable for processing the compositions. Thus, the compositions described herein may be formulated in many different manners, such as for injection or infusion by intravenous, intraarterial, intradermal, intramuscular, intracerebral, intraperitoneal, intracerebrospinal, subcutaneous, intraocular, intraarticular, intrasynovial, or intrathecal routes, for oral, buccal, sublingual, nasal, topical, transdermal, ophthalmic, vaginal, rectal, intravesical, pulmonary administration, and/ or by various controlled-release systems, such as immediate release, delayed release, or sustained release systems.

Additional agents such as adjuvants or further pharmaceutically active agents may be included in the compositions described herein, such as vitamins, anti-inflammatory agents, analgesics, muscle relaxants, and so on. Such active agents may include drugs or pharmaceuticals or nutraceuticals having therapeutic and/or nutritional value and include, but are not limited to members of classes of actives including analgesics, anti-inflammatory agents, anthelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac ionotropic agents, corticosteroids, diuretics, anti-parkinsonian agents, gastro-intestinal agents, histamine receptor antagonists, keratolytics, lipid regulating agents, antianginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents anti-obesity agents, cognition enhancers, anti-urinary incontinence agents, nutritional oils, anti-benign prostate hypertrophy agents, essential fatty acids, non-essential fatty acids and the like.

Specific pharmaceutical active agents include but are not limited to: acetaminophen; acyclovir; acetyl cysteine; acetylcholine chloride; alatrofloxacin; alendronate; alglucerase; alfuzosin; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaphlat; enkephalin; enoxacin; enoxaphn sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; hepatitis A virus vaccine inactivated; hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; Japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; mizolastine; methanamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolaphl; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine;

vinorelbine; vitamin B12; warfarin sodium; yellow fever vaccine; zalcitabine; zanamavir; zolandronate; zidovudine; and pharmaceutically acceptable salts, isomers and derivatives thereof.

Useful pharmaceutical active agents further include but are not limited to aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine,clonazepam, clopidogrel, codeine, coenzyme Q10, cyclobenzaprine, cyclosporin, danazol, dantrolene, dexchlorpheniramine, diazepam, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, hydrochlorothiazide, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lorazepam, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, terbutaline tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, Zolpidem, zopiclone, and pharmaceutically acceptable salts, isomers and derivatives thereof.

Further, useful pharmaceutical active agents include cytokines, peptidomimetics, peptides, proteins, toxoids, serums, antibodies, vaccines, nucleosides, nucleotides, portions of genetic material, nucleic acids, and the like. Useful nutraceuticals include but are not limited to: vitamins such as carotenoids, vitamin E, vitamin D, vitamin C, thiamine, riboflavin, niacin, folic acid, pyridoxine, biotin, pantothenic acid, cyanocobalamin and the like; minerals such as magnesium, manganese, zinc, selenium, chromium, copper and the like; and nutritional elements such as alpha lipoic acid, lutein, beta carotenoids, and the like.

The compositions described herein may find particular use in the form of an inhalable dry powder formulation, which may comprise a pharmaceutically acceptable carrier or excipient. It will be understood that "dry powder" refers to a fine particulate composition that is not suspended or dissolved in a propellant, carrier, or other liquid. It is not meant to necessarily imply a complete absence of all water or liquid molecules.

The inhalable dry powder formulation is, in aspects, provided to the patient by pulmonary inhalation using a dry powder inhalation system. In one aspect, the system comprises a dry powder inhaler with or without a container and a dry powder formulation.

In another aspect, the composition described herein is for pulmonary administration by inhalation using a breath powered, dry powder inhaler with or without a container, wherein the container can be a cartridge, such as a unit dosing cartridge for a reusable inhaler, or a single use inhaler. In this and other aspects, the dry powder inhaler system typically comprises a high resistance dry powder inhaler having air flow resistance values through its conduits in use of about 0.0065 to about 0.200 √(kPa)/L per minute, wherein the dry powder inhaler in use has an air flow distribution of from about 10% to about 30% through the container, which generates peak inhalation pressure differentials of about 2 kPa to about 20 kPa, and peak flow rates of between 7 L to about 70 L per minute.

The dry powder formulation is a stable composition and can comprise microparticles which are suitable for inhalation and which dissolve rapidly in the lung and rapidly deliver the composition described herein to the pulmonary circulation. Suitable particle sizes for pulmonary administration are typically less than 10 µm in diameter, and more typically less than 5 µm. Exemplary particle sizes that can reach the pulmonary alveoli range from about 0.5 µm to about 5.8 µm in diameter. Such sizes refer particularly to aerodynamic diameter, but often also correspond to actual physical diameter as well. Such particles can reach the pulmonary capillaries and can avoid extensive contact with the peripheral tissue in the lung. In this aspect, the drug can be delivered to the arterial circulation in a rapid manner and avoid degradation of the active ingredient by enzymes or other mechanisms prior to reaching its target or site of action in the body. In one aspect, dry powder compositions for pulmonary inhalation can comprise microparticles wherein from about 35% to about 75% of the microparticles have an aerodynamic diameter of less than 5.8 µm.

In one aspect, the formulation comprising the composition described herein can be administered to a subject in a dry powder formulation by inhalation using a dry powder inhaler such as the inhaler disclosed, for example, in U.S. Pat. No. 7,305,986 and U.S. patent application Ser. No. 10/655,153 (US 2004/0182387), which are incorporated herein by reference. Repeat inhalation of the dry powder formulation can also be administered once, twice, three, four, or more times a day as needed.

Methods of Administration and Treatment

It has now been found that a whole-plant cannabis extract can be approximated by combining at least two extracts from different cannabis plant tissue sources and optionally mixing those with an oily carrier, such as hemp seed oil. In aspects, these different extracts, administered in combination, exert a synergistic effect in terms of symptom relief in various conditions such as multiple sclerosis and can therefore be used to treat the symptoms of certain conditions, such as multiple sclerosis, in synergistic combination.

It will be understood that the different cannabis plant tissue sources may be comprised of different portions of the same plant or same strain, such as a sinsemilla extract and a trim extract of the same cannabis strain, for example. It will also be understood that the different cannabis plant tissue sources may comprised of the same or different portions of different plants or strains. For example, in one aspect, a sinsemilla extract from one strain may be combined with a trim extract from another strain. In another aspect, a sinsemilla extract of one strain may be combined with a sinsemilla extract of another strain.

The condition to be treated by the compositions described herein may be any condition associated with the cannabinoid system and/or known to be treatable with cannabis, such as, for example, arthritis, sleep conditions, spasticity, restless leg syndrome, stiffness, post-traumatic stress disorder, Alzheimer's disease, schizophrenia, depression, alcoholism, Parkinson's disease, stroke, premature labor, endotoxic shock, hepatic cirrhosis, atherosclerosis, cancer, bone implantation, glaucoma, emesis, pain, multiple sclerosis, amyotrophic lateral sclerosis, encephalitis, Huntington's disease, obesity, feeding, fasting, stress, memory, aging, hypertension, cirrhosis, septic shock, cardiogenic shock, cerebral ischemia, myocardial infarction, neurotoxicity, febrile seizures, various intestinal disorders, nausea and vomiting associated with cancer chemotherapy, and AIDS-related cachexia.

The compositions of the invention can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the compositions of the invention are administered orally, intradermally, sublingually, intrarectally, or by inhalation. More typically, the compositions of the invention are administered orally.

The compositions of the invention may, in aspects, be administered in combination, concurrently or sequentially, with conventional treatments for the condition in question, including with analgesics, anti-inflammatories, or muscle relaxants, for example. The compositions of the invention may be formulated together with such conventional treatments when appropriate.

The compositions of the invention may be used in any suitable amount, but are typically provided in doses comprising from about 0.1 to about 1000 mg of active agent, e.g., THC, CBD, a particular terpene, or another cannabinoid. For example, typical doses per tablet or capsule for oral administration comprise from about 0.1 to about 10 mg THC, such as from about 1 to about 5 mg THC, such as from about 1 to about 3 mg THC, such as about 1.5 mg THC.

Additionally, treatment with the compositions described herein may occur once or may be repeated several times. For example, treatment may occur as needed, several times daily, weekly, monthly, yearly, or a combination thereof, depending upon the disease state. For example, a subject may be administered several doses per day to treat active and acute symptoms. Once the symptoms improve, follow-up maintenance doses may be provided on an as-needed basis. Typically, administration would be two to four times daily.

While it has been stated above that the compositions described herein can be used to treat symptoms, it will be understood that they could also be used to prevent symptoms from occurring.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Preparation of an Encapsulated Whole-Plant Cannabis Extract

Dried Sinsemilla Extraction:

100 g of dried sinsemilla were milled to a fine powder and transferred to a 1 L Erlenmeyer flask. A stir bar was added and the flask and it was set on a magnetic stirring plate. 800 mL of ice-cold 99:1 isopropanol:water were added to the flask. The magnetic stirring was set to the smallest speed that maintained the cannabis in suspension. The extraction was carried out for 3 minutes.

The mixture was quantitatively transferred, and vacuum filtered through medium porosity filter paper, and washed three times with 20 mL of ice-cold 99:1 isopropanol:water. The filtrate was quantitatively transferred and vacuum filtered through a fine frit glass funnel. The debris collected in these filtrations were discarded, but may be set aside for additional extraction steps and/or analytical chemistry.

The filtrate was evaporated in an appropriately-sized container in a fume hood, on a hot-plate, with the minimum heat necessary to sustain very gentle boiling of the solvent. In alternative preparations, the filtrate may have been additionally adjusted, diluted, extracted, filtered, centrifuged, etc., prior to evaporation. Upon incipient dryness, the container was removed from the heat, allowing the remaining mixture to go dry as gently as possible. The resulting oil was the sinsemilla extract. It was withdrawn into 5 ml Hamilton syringes and stored at 4° C. until use.

Trim Extraction:

The trim extraction was carried out identically to the dried sinsemilla extraction, except that the starting material was finely ground, dried, cannabis leaf, especially those leaves which were found in the vicinity of the sinsemilla.

Preparation of the Whole Plant Extract:

One ml of the dried sinsemilla extract was ejected from its Hamilton syringe into a 50 ml beaker. Additionally, 1.5 mL of the trim extract was ejected from its Hamilton syringe into the same 50 mL beaker. A stir bar was added to the beaker, and it was set on a magnetic stirrer. Additionally, 20 mL of commercially-sourced hemp seed oil was added by volumetric pipet to the beaker. The beaker's contents were made to stir gently until the mixture was homogeneous. The resulting mixture is the whole-plant extract. A one ml aliquot of the whole plant extract was set aside for analytical chemistry. Typical analyses are ~14 mg/mL THC and 4.8 mg/mL CBD.

Preparation of the Drug Formula:

The whole plant extract was transferred to the previously tared plastic container of an Unguator® electronic mortar and pestle. The combined mass of the plastic container and the whole plant extract was determined to be 18.134 g. To this was added 27.184 g of maltodextrin (dextrose equivalent 20) and 27.189 g of microcrystalline cellulose NF (PH 105). These ingredients were mixed in the Unguator for 2 minutes to afford the formula.

Encapsulation:

The resulting powder was transferred to ~180 #1 capsules using a capsule filling machine. Each capsule accommodated about 390 mg of the powder, and contained ~1.5 mg THC and ~0.5 mg CBD.

Example 2—Analytical Chemistry of a Combined Sinsemilla and Trim Extracts

Analysis was carried out using the Cannalytics® (Greenwood Village, Colo.) "Cannabis Analysis Test" kit.

50 mg of combined sinsemilla and trim extracts were diluted in a 1.5 mL Eppendorf tube, with 1 mL of the proprietary "test fluid" provided with the kit. The Eppendorf tube was thoroughly mixed by multiple inversions, and allowed to sit for two minutes.

As shown in FIG. 1, Four spots, A-D from left to right, were made at the bottom of the proprietary TLC plate provided with the kit. Spots A and C were each made with a capillary tube provided with the kit and calibrated to withdraw 2 μL of sample. Each capillary tube was used only once. Spots B and D were each made with two applications of a capillary tube. One capillary tube was used for each of spots B and D (i.e., each capillary tube was used twice). Thus spots A and C each represent 2 μL of sample, spots B and D each represent 4 μL of sample. The plate was allowed to dry in a fume hood for 10 minutes.

Spots B and C were then gently heated over a small, low-temperature (i.e., orange) flame from a cigarette lighter, for 10 seconds. The plate was then allowed to cool in a fume hood for 2 minutes.

The developing chamber provided with the kit was filled with 2 mL of the "test fluid" provided with the kit. The plate was placed in the developing chamber, and the chamber was closed with the lid provided. The plate was allowed to develop for 23-25 minutes, until the solvent had reached, but not exceeded, the top of the plate. The plate was then removed from the developing chamber and allowed to dry for 3 minutes in a fume hood.

The plate was placed against a disposable piece of cardboard at the rear of the fume hood, which was angled about 30° from the vertical. From about 30 cm away, a previously prepared solution of the proprietary colouring solution, prepared as per the instructions in the kit, was sprayed against the plate. The plate was allowed to dry in the fume hood for 5 minutes.

Spot intensities were immediately evaluated against the calibrated spot intensities derived from solutions of known cannabinoid concentrations which were provided on a card included in the kit. These provide weight percentages (mg/mg) of cannabinoids in the sample.

In the representative example shown below, THC was present at about 37% by weight, and CBD was present at about 3% by weight.

Example 3—Case Studies Following Treatment with the Composition of Example 1

Case Study 1:

A female patient in her mid-50s who had been diagnosed with osteoarthritis, whose condition was characterized by "bone on bone contact," and who was waiting for scheduled hip replacement surgery, had previously been consuming 30 mg THC/10 mg CBD four times daily, dissolved and delivered in hemp seed oil. An hour after taking two capsules (total: 3 mg THC, 1 mg CBD) of the formulation described in Example 1 she was pain free for the following 6 hours, at which point she consumed another two capsules and her pain relief was extended until she went to bed. This patient has been following the above treatment regimen for two weeks, with continued, satisfactory, results.

Case Study 2:

A male patient in his mid-50s who had been diagnosed with Progressive Relapsing Multiple Sclerosis, who had previously been wheelchair-bound, and who had previously been living a "normal life" (outside of a wheelchair) consuming 30 mg THC/10 mg CBD four times daily, dissolved and delivered in hemp seed oil, has experienced similar relief from 4 capsules in each 24 hour period (total: 6 mg THC, 2 mg CBD).

Case Study 3:

A wheelchair-bound male patient in his mid-30s with a spinal cord injury, debilitating and painful chronic muscle spasms, and nighttime restless leg syndrome typically used 5 to 7 grams of dried cannabis a day to control the pain. He used two capsules prepared as per Example 1 and was pain free for 6 hours. Additionally he reported significant improvement in sleep as a consequence of reduced restless leg syndrome. This formulation permitted him to reduce his dried cannabis consumption by about 2 g daily.

Example 4—Placebo-Controlled Double-Blind Multiple Sclerosis Trial Using the Composition of Example 1

Background:

In a manner unknown to the principal investigator, ten medical cannabis patients with diagnoses of multiple sclerosis were divided, five each, into Genuine and Placebo groups. Patients in the Genuine Group were asked to take three capsules daily containing the composition of Example 1, with each capsule containing about 3 mg THC and 1 mg CBD. The Placebo Group was asked to take capsules prepared identically, but in which only hemp seed oil was found, but no combined extract. The study lasted two weeks. Patients were asked to cease using whatever other edible or topical cannabis preparations they may have been consuming for the duration of the study. Additionally, they were asked to monitor their consumption of smoked cannabis during the study, particularly whether it seemed to increase or seemed to decrease.

Patients were interviewed prior to participation and administered a pain questionnaire in which they described a variety of aspects of their pain, including its intensity, its location, its apparent depth, its apparent sharpness and dullness, etc. Every other day throughout the trial patients were contacted and asked to rate their pain within the previous 24 hours, according to the same criteria.

The Genuine Group consisted of:
(a) a middle aged male with primary progressive MS, diagnosed for the past 12 years. Current treatment: medical cannabis, smoked using a bong, 4 times a day, 3 bowls at a time. Experiences hip, back, and leg pain, with difficulty walking,
(b) a late teens male with MS, diagnosed for the past 2 years. Current treatment: medical cannabis, smoked. Experiences leg pain,
(c) an older female (grandmother) with MS, complicated by trigeminal neuralgia, diagnosed for the past 21 years. Current treatment: 600 mg/day of gabapentin, supplemented by medical cannabis oil at night. Experiences hip pain, requires the use of a walker, and is increasingly wheel-chair bound. Pain is well controlled under the current regimen, however, and flares up only sporadically, perhaps 3 times/year, and
(d) a mid-forties female, age unknown, with MS, diagnosed for the past 30 years. Experiences no pain, but severe spasticity in her legs. Has been on rebif and had venoplastic surgery but experienced no relief of symptoms. Current treatment: home-made medical cannabis extract in glycerol, about 1:1 THC/CBD. Current treatment keeps spasticity under control.

The Placebo Group consisted of:
(a) a male, age unknown, diagnosed with MS since 2004, who complains of pain in a "bear hug" across his chest, back and shoulder pain, and weakness. Current treatment: medical cannabis, vaped, and in capsules,
(b) a woman, age unknown, diagnosed with relapsing remitting MS, who complains of pain on her left side. Current treatment: aubagio, supplemented by medical cannabis in a variety of forms, (c) a woman, age unknown, diagnosed with MS complicated by trigeminal neuralgia, occipital genticular neuralgia, PTSD and anxiety. She complains of pain associated with her right side and back, going up to the head, and around the face. Current treatment: Botox injections, medical cannabis smoked throughout the day and extracted in coconut oil, in capsules, (d) a woman, age unknown, diagnosed with MS for the past 10 years, who complains of leg pain and spasticity. Current treatment: Cannamed 113 (high CBD) during the day to control spasms, high THC at night. Previously took lyrica, and (e) a woman, age unknown, diagnosed with MS since 2000, complicated by IBS, osteopenia, trigeminal neuralgia, optic neuritis, who complains of "atlas pain." Current regimen: tegretol supplemented by medical cannabis tincture.

Results:

Three of the four patients who remained in the Genuine Group experienced relief of their pain and—in some cases—also spasticity associated with MS, while taking the capsules. The fourth patient, who consumed her own homemade capsules at the same time as she was taking the study capsules, experienced neither a worsening nor an improvement in her condition in the course of the study.

Figure 2:
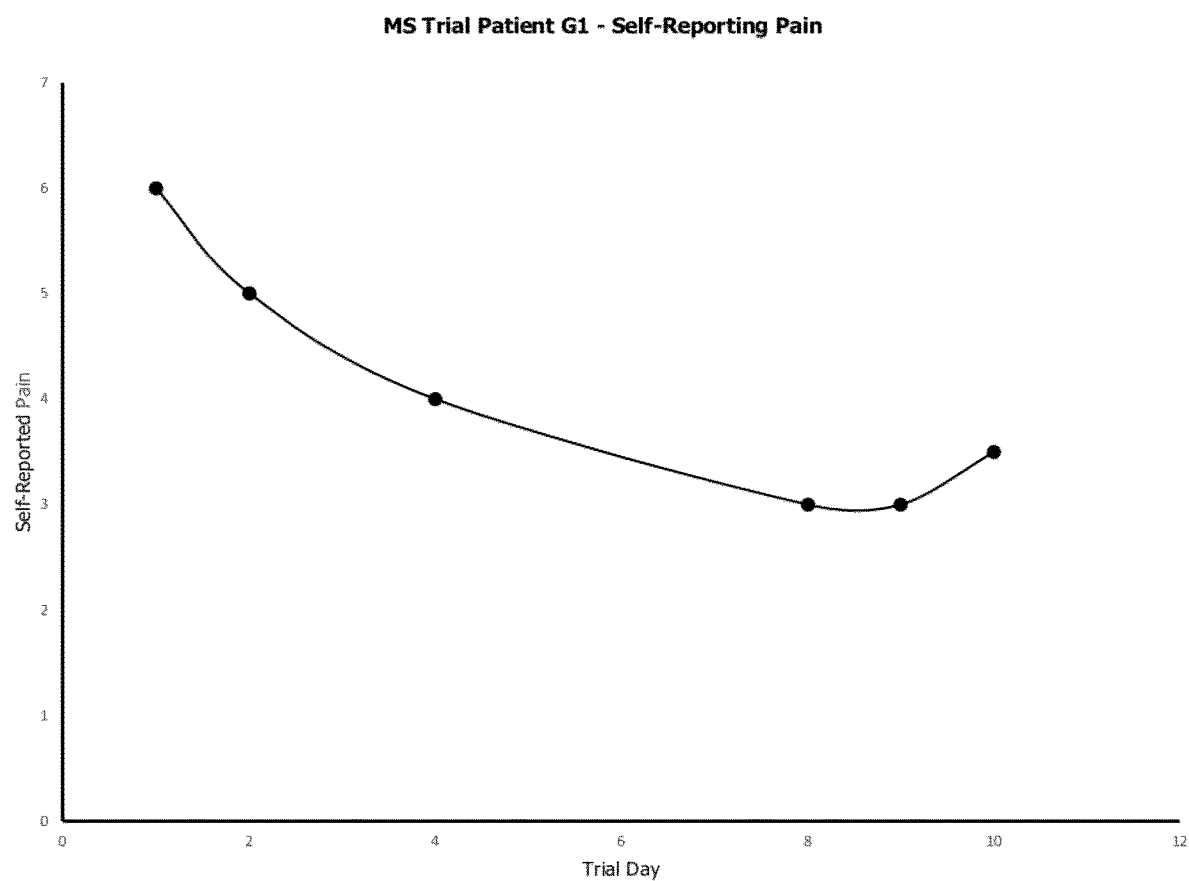
FIG. 2 shows a chart of self-reported pain levels for patient G1, being treated with the composition described herein.
Figure 3:
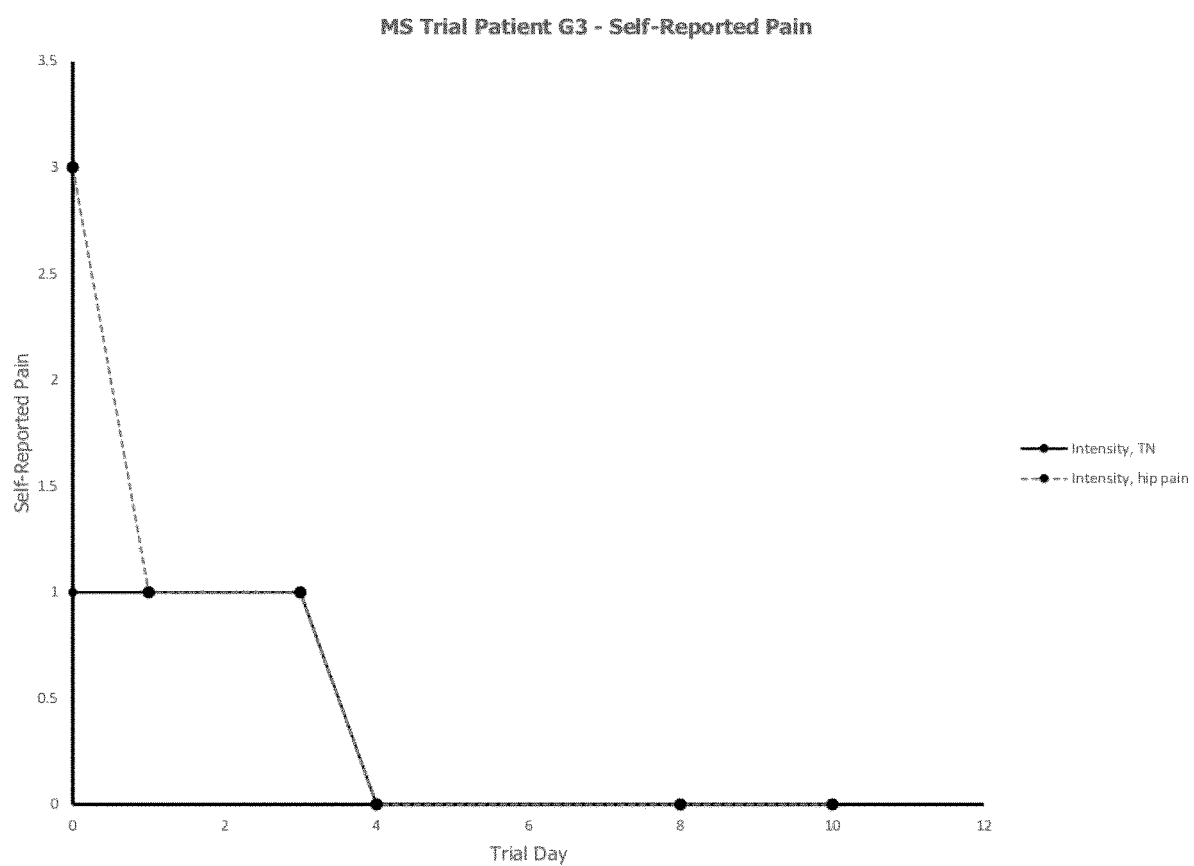
FIG. 3 shows a chart of self-reported pain levels for patient G3, being treated with the composition described herein.
Figure 4:
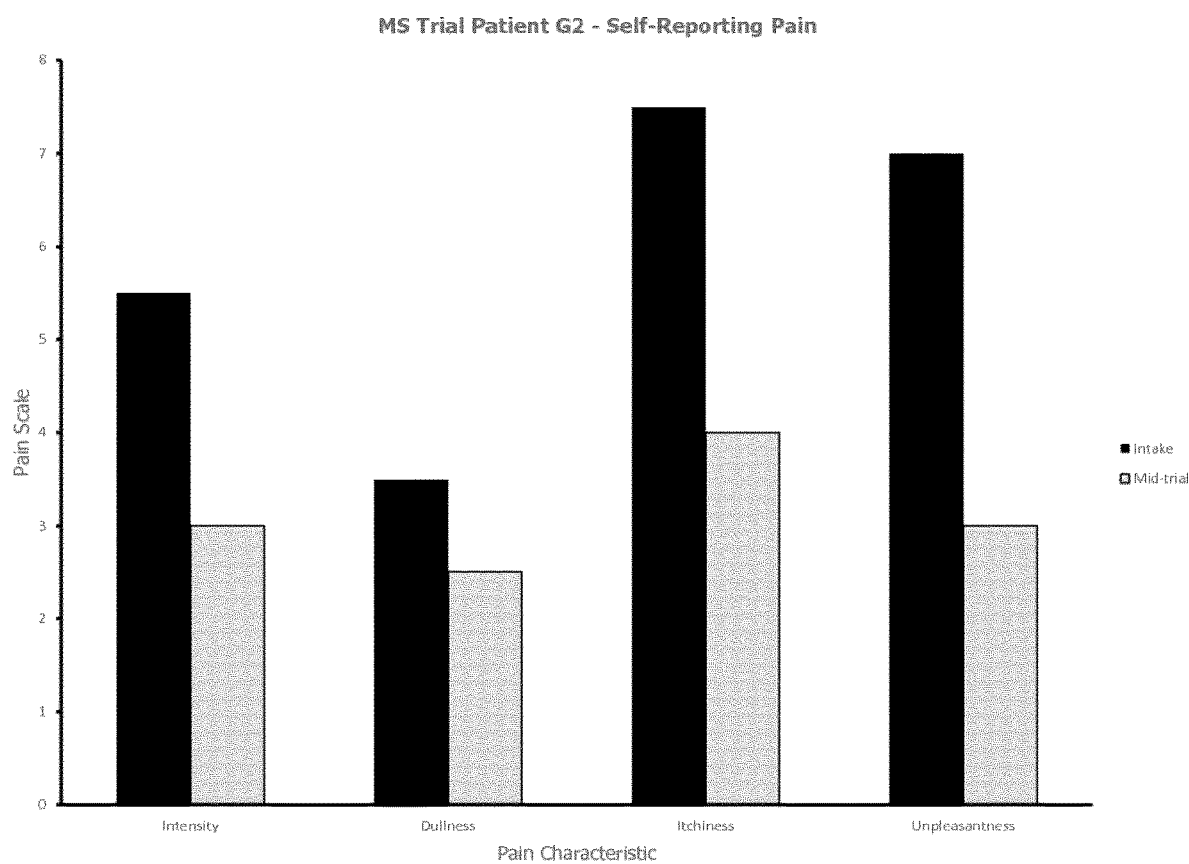
FIG. 4 shows a chart of self-reported pain levels for patient G2, being treated with the composition described herein.

FIGS. 2 and 3 clearly indicate the downward trend in the self-reported intensity of pain over the course of the investigation, for participants G1 and G3, respectively, of the Genuine Group. FIG. 4 shows four pain characteristics which declined, in the course of the study, for patient G2, of the Genuine Group.

Figure 5:
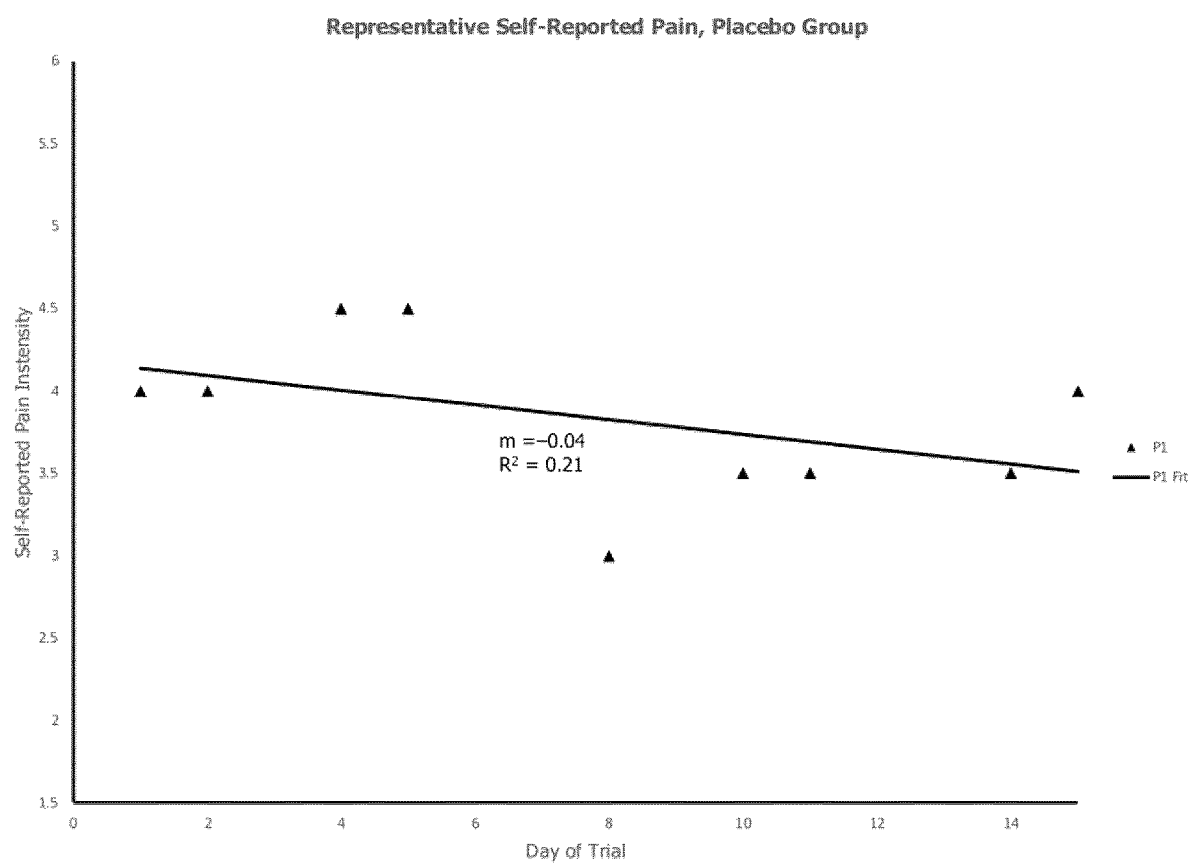
FIG. 5 shows the typical slope and scatter of a line describing the pain evolution of a patient receiving placebo.

In the Placebo Group, in contrast, the self-reported pain measurements were, for all participants, highly scattered about a mean, without clear increasing or decreasing trends. Linear regressions of these pain profiles all had slopes near zero, with small goodness-of-fit ($R^2$) values; this is the expected result for the placebo under conditions in which the patient may supplement by dosing with smoked cannabis—that is, neither a worsening, nor an improvement, in the patient's condition. For each regression, these slopes and $R^2$ values are reported in Table 1. To provide an idea of the character of scatter in typical Placebo Group profiles, a representative plot is provided in FIG. 5. Note that Placebo-Group Patient 2 did not provide enough data for analysis.

TABLE 1

$R^2$ values for pain profiles.

| Patient | Slope | $R^2$ |
|---------|---------|---------|
| 1 | −0.045 | 0.20985 |
| 3 | −0.0319 | 0.0228 |
| 4 | 0.03571 | 0.00735 |
| 5 | −0.0775 | 0.2584 |

Other Medically Relevant Observations:

Two Genuine Group patients noted improvements with respect to itchiness during the trial. One Genuine Group patient suggested that the composition of Example 1 was at least as effective, if not more effective, than the 600 mg/day of gabapentin she had been prescribed.

Summary:

Three out of the four Genuine Group Patients experienced clear relief of pain while taking capsules as prepared in Example 1. Some patients indicated improvements in the muscular spasticity associated with MS. Four out of four responding Placebo Group patients reported no improvement in their symptoms, or a worsening of their symptoms while taking Placebo.

Example 5—Case Studies: Dose Dependence in Case Studies of Arthritis

Background:

Medical cannabis patients complaining of arthritis were assembled to participate in case studies to evaluate dose-dependent effects of administering the composition of Example 1. Patients were instructed to take two capsules daily in the first week of the study, three capsules daily in the second, and four capsules daily in the third. Patients were asked to rate their pain, their consumption of smoked cannabis, and describe other aspects of their pain and quality of life—on a daily basis throughout the study.

Results:

Of six original patients, four provided data of sufficient quality to be analysed. Of these, three experienced relief of pain in a manner consistent with dose-dependence; the fourth person's condition was neither improved nor worsened during the study (data not shown).

Figure 6:
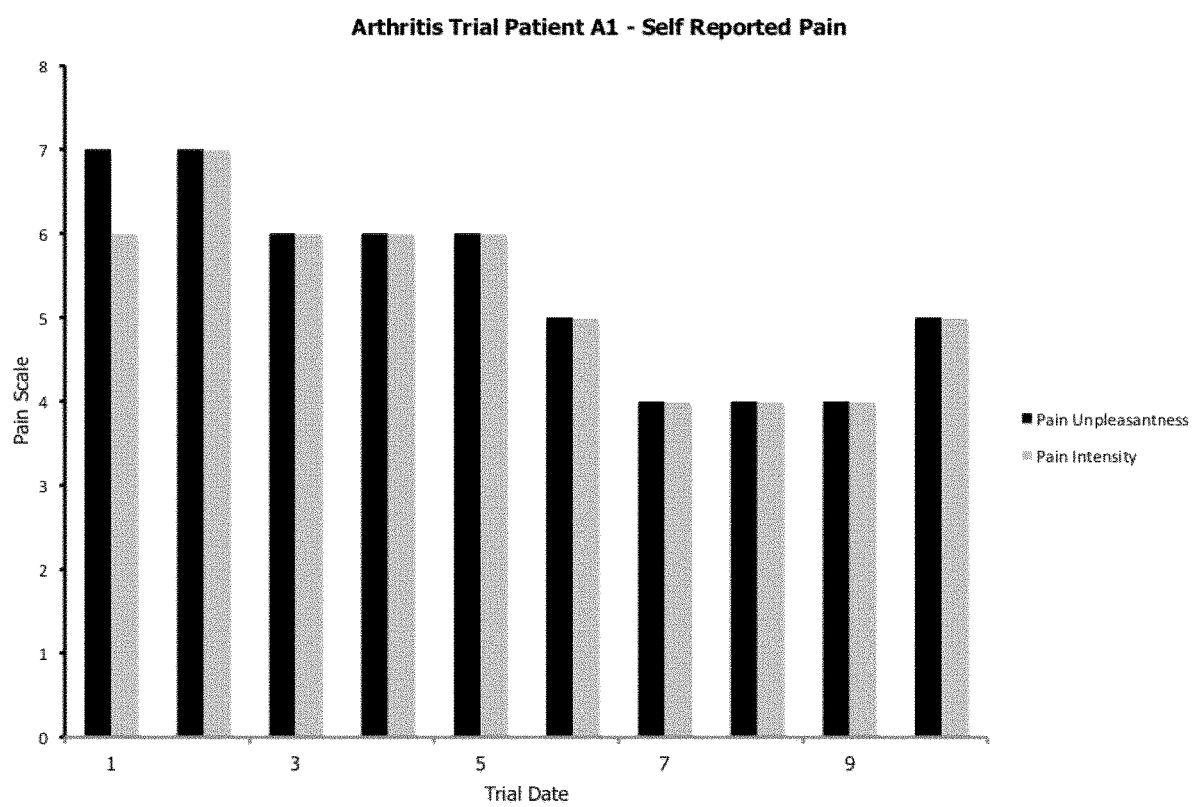
FIG. 6 shows a chart of self-reported pain levels for patient A1, being treated with the composition described herein.

Patient A1 was a 55 year old male suffering from limited mobility due to multiple fused vertebrae, and concomitant pain in his back, shoulders, and neck, and generally, as well as poor sleep and exhaustion. His typical treatment regimen consisted of significant dabbing. He reported lackluster results for the lower, earlier, numbers of capsules per day. But, note that at day 7 in FIG. 6, the point at which he began to take four capsules per day, his pain decreased and remained lower.

Figure 7:
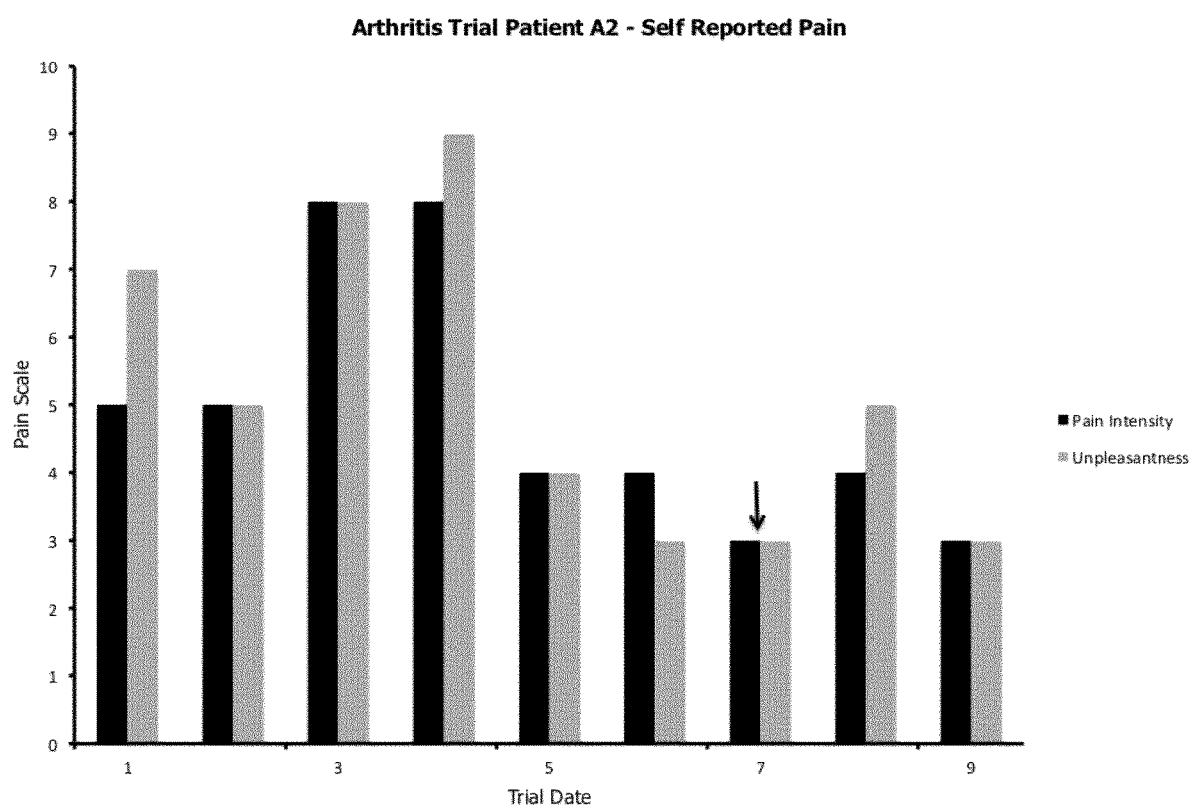
FIG. 7 shows a chart of self-reported pain levels for patient A2, being treated with the composition described herein.

Patient A2 was a 53-year-old male in "reasonable shape for someone with restricted walking abilities," who suffered post-injury arthritis in his neck and shoulders. FIG. 7 shows the progress of his self-reported pain over the course of the study, and indicates a clear downward trend. The patient noted that the spike in unpleasantness at the second-to-last date was associated with unrelated pancreatic symptoms. The arrow indicates the point at which the patient began to take 4 capsules a day.

Figure 8:
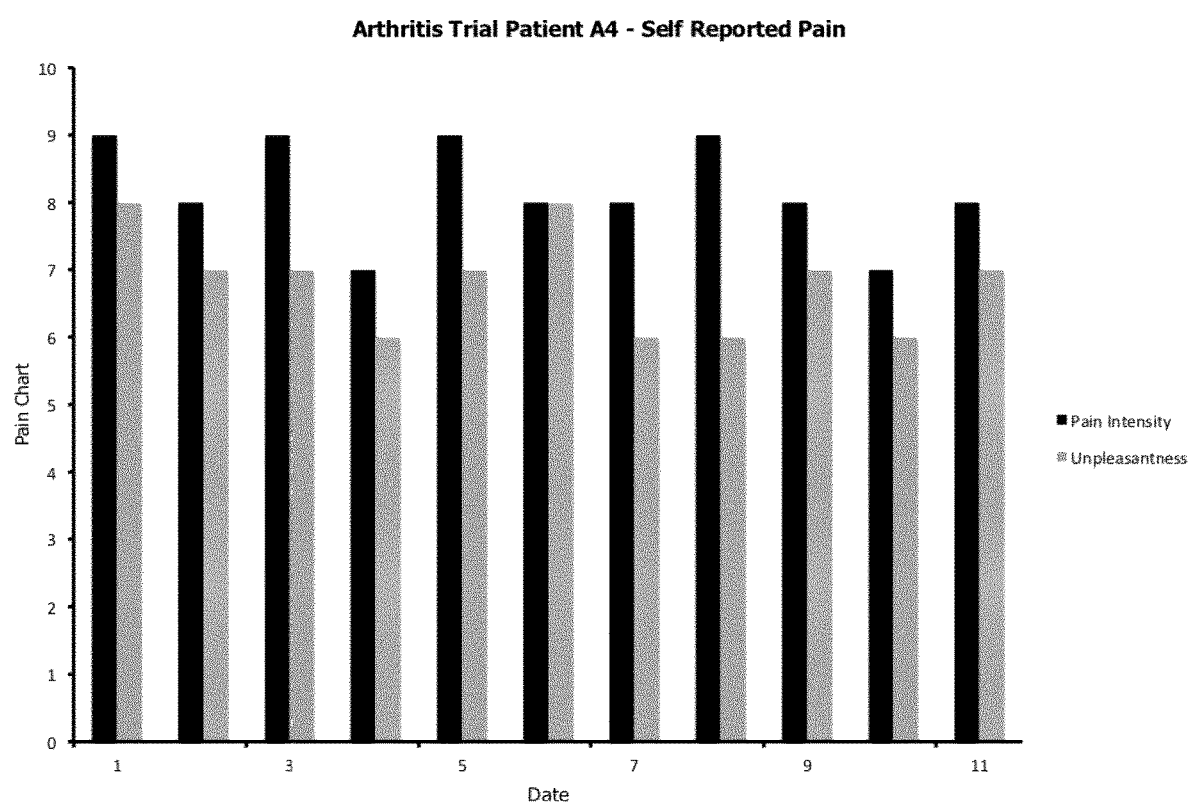
FIG. 8 shows a chart of self-reported pain levels for patient A4, being treated with the composition described herein.
Figure 9:
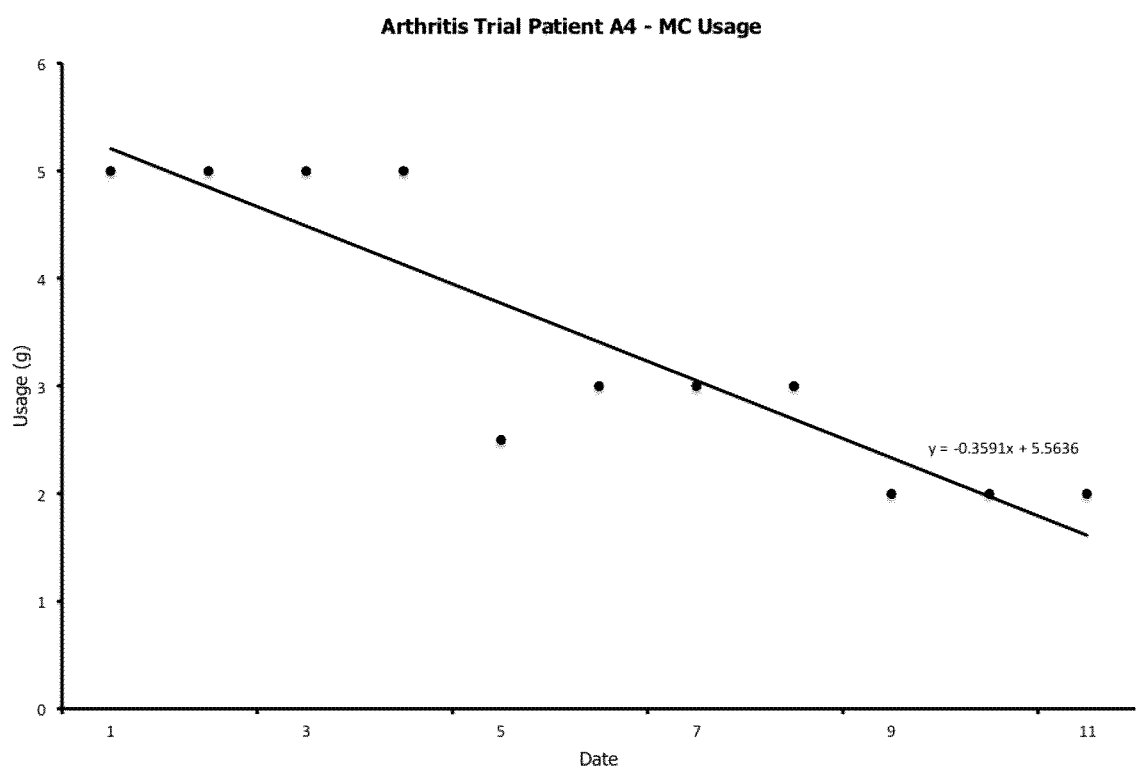
FIG. 9 shows a chart of smoked medical cannabis usage for patient A4, being treated with the composition described herein.

The evidence of dose-dependence provided by patient A4 was of a slightly different character. This patient, a 63 year-old-male suffering background arthritis pain at all times, but who was otherwise in good health and physically fit noticed no particular improvement in his pain over the course of the trial. However, over the course of the trial, as his dose increased, his consumption of cannabis by smoking (dabbing) declined steadily. The consistency of this patient's pain is presented in FIG. 8; his decline in medical cannabis consumption is presented in FIG. 9.

Example 6—Cannabinoid and Terpene Profiles of Combined Bud and Trim Extracts Sourced from a Variety of Cannabis Strains A set of three different combined extracts, prepared as in Example 1, were prepared: PK Oil 04171, PC Oil 04172, and MX Oil 05171. The source cannabis materials for these preparations were, respectively, Pineapple Kush bud and trim, Purple Chemdawg bud and trim, and bud and trim assembled from two other strains. The combined extracts were sent for cannabinoid and terpene analysis to RPC, 921 College Hill Rd, Fredericton NB, Canada E3B 6Z9, www.r-pc.ca. Selected results of these analysis are presented in Tables 2 and 3.

TABLE 2

Cannabinoids present in three different combined extracts.
Cannabinoids in marijuana oil by HPLC

| RPC Sample ID | | | 233900-1 | 233900-2 | 233900-3 |
|---|---|---|---|---|---|
| Client Sample ID | | | PK Oil 04171 | PC Oil 04172 | MX oil 05171 |
| Date Sampled | | | Apr. 26, 2017 | Apr. 29, 2017 | May 1, 2017 |
| Matrix | | | oil | oil | oil |
| Analytes | Units | RL | | | |
| Δ-9-Tetrahydrocannabinol | % | 0.05 | 56.8 | 58.3 | 23.4 |
| Cannabidiol (CBD) | % | 0.05 | 0.05 | 0.06 | 1.55 |
| Cannabigerol (CBG) | % | 0.05 | 6.08 | 6.02 | 1.17 |
| Cannabinol (CBN) | % | 0.05 | 0.50 | 1.00 | 2.04 |
| Cannabichromene (CBC) | % | 0.05 | 2.63 | 0.82 | 0.10 |
| Δ-9-Tetrahydrocannabinol$_{total}$ | % | 0.07 | 57.2 | 58.4 | 23.4 |
| Total Cannabidiol (CBD) | % | 0.07 | <0.07 | <0.07 | 1.59 |
| Total Cannabigerol (CBG) | % | 0.07 | 8.00 | 6.98 | 1.17 |

TABLE 3

Terpenes present in three different combined extracts.
Terpenes in marijuana oil

| RPC Sample ID | | | 233900-1 | 233900-2 | 233900-3 |
|---|---|---|---|---|---|
| Client Sample ID | | | PK Oil 04171 | PC Oil 04172 | MX oil 05171 |
| Date Sampled | | | Apr. 26, 2017 | Apr. 29, 2017 | May 1, 2017 |
| Matrix | | | oil | oil | oil |
| Analytes | Units | RL | | | |
| Alpha pinene | % | 0.01 | <0.01 | <0.01 | <0.01 |
| Beta pinene | % | 0.01 | <0.01 | <0.01 | <0.01 |
| Myrcene | % | 0.01 | <0.01 | <0.01 | <0.01 |
| Limonene | % | 0.01 | 0.02 | 0.01 | <0.01 |
| Terpinolene | % | 0.01 | <0.01 | <0.01 | <0.01 |
| Linalool | % | 0.01 | 0.0 | 0.0 | <0.01 |
| Terpineol | % | 0.01 | 0.04 | 0.04 | <0.01 |
| Caryophylene | % | 0.01 | 0.67 | 0.59 | 0.02 |
| Humulene | % | 0.01 | 0.31 | 0.27 | <0.01 |

These analyses indicate that the compositions derived from Pineapple Kush and Purple Chemdawg are highly similar with respect to their primary cannabinoids. Both have high THC levels of about 57 wt %, and are largely devoid of cannabidiol. They have similar levels (~6 wt %) of cannabigerol, and small levels of cannabinol (0.5% and 1%). PK is moderately enriched in cannabichromene.

As the total concentration of THC is equal to the sum of its acidic and decarboxylated forms (THC$_{total}$=THC+ THCA, in which THCA is the level of acidic form of THC), because the values of THC and THC$_{total}$ are similar, it is evident that most THC has been decarboxylated, and this is probably also true for all other cannabinoids.

In contrast to the PK- and PC-derived compositions, the MX composition has about half the THC content as the others, but it is substantially enriched in cannabidiol, although the overall level of cannabidiol is still small, at ~1.5 wt %. As with the others, the data suggest that cannabinoids have been decarboxylated.

With respect to their terpene profiles, all three compositions have low levels of terpenes, although caryophyllene and humulene are present in the PK and PC compositions.

Figure 10:
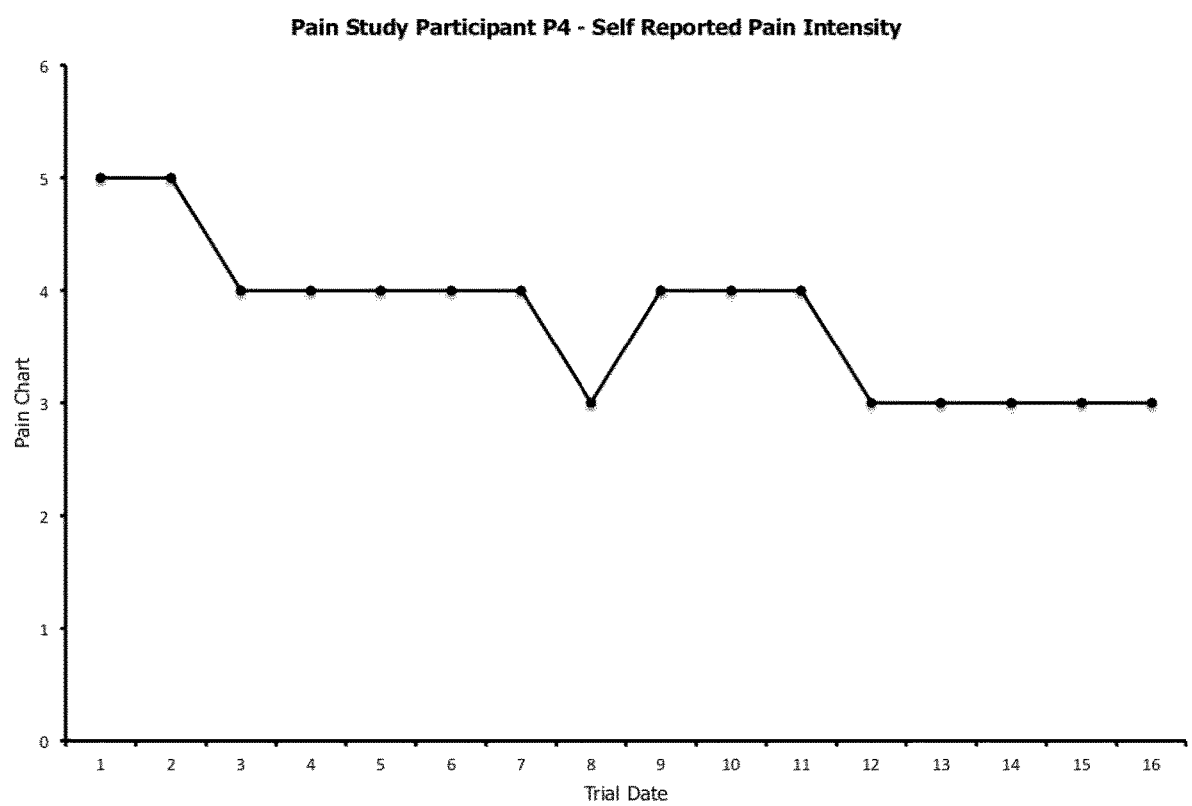
FIG. 10 shows a chart of self-reported pain levels for patient P4, being treated with the composition described herein.
Figure 11:
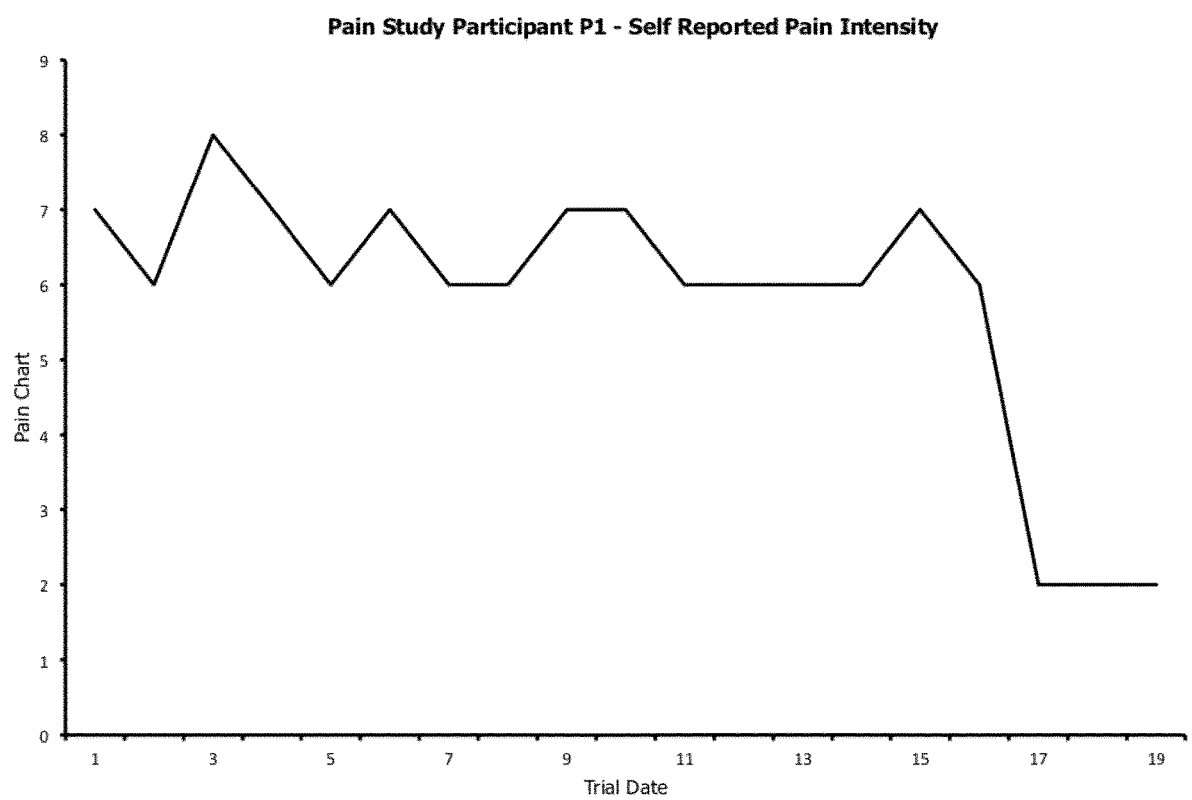
FIG. 11 shows a chart of self-reported pain levels for patient P1, being treated with the composition described herein.

Example 7—Differential Effectiveness of Example 1 Compositions Derived from Different Cannabis Strains Patients in this study were administered PK compositions in week 1, PC compositions in week 2, and MX compositions in week three. Two patients clearly indicated that the MX derived medication, administered in the third week of the study, was superior to the compositions administered earlier in the study. One, patient P4, experienced a general decline in pain over the course of the three week trial, exhibiting the least pain in the third week. Another, patient P1, experienced a precipitous decline in pain during the third week of the study. These data are presented in FIGS. 10 and 11, respectively.

The most obvious differences between the MX composition and the PK and PC compositions are the relative decrease in THC content and the relative increase in CBD content. In this case, it is perhaps the additional CBD that affords the improved pain relief.

Data from PTSD patients also suggests different effects of compositions from different strains, although these are more difficult to interpret in terms of the available chemical analyses. In any case, two PTSD patients were involved in the evaluation of the compositions of Example 1 derived from three different cannabis strains. These patients were asked to respond daily using a standard measurement tool for PTSD symptoms. With respect to symptoms relating to memory of the stressful experience, self-esteem, self-blame, the prevalence of negative emotions, and similar issues, both patients reported their lowest scores while using the strains derived from Purple Chemdawg. Scores were calculated according to the standard instructions for the DSM-V measurement tool. These data are presented in Table 4, below.

TABLE 4

PC Strain Provides Superior Relief of PTSD Criteria D Symptoms

| PATIENT | Strain | CRITERION D |
|---|---|---|
| PTSD1 | PK | 90 |
| PTSD1 | PC | 77 |
| PTSD1 | MX | 95 |
| PTSD2 | PK | 120 |
| PTSD2 | PC | 70 |
| PTSD2 | MX | 73 |

Given the number of cannabinoids, their potential for synergistic effects, and the number of terpenes, and the variety of their medically relevant effects, and, in light of the data presented here, the space of potential of preparing unique compositions tailored to specific medical complaints afforded by the compositions described herein is clearly enormous.

Example 8—Decrease in the Consumption of Smoked Cannabis while Using the Composition of Example 1

Figure 12:
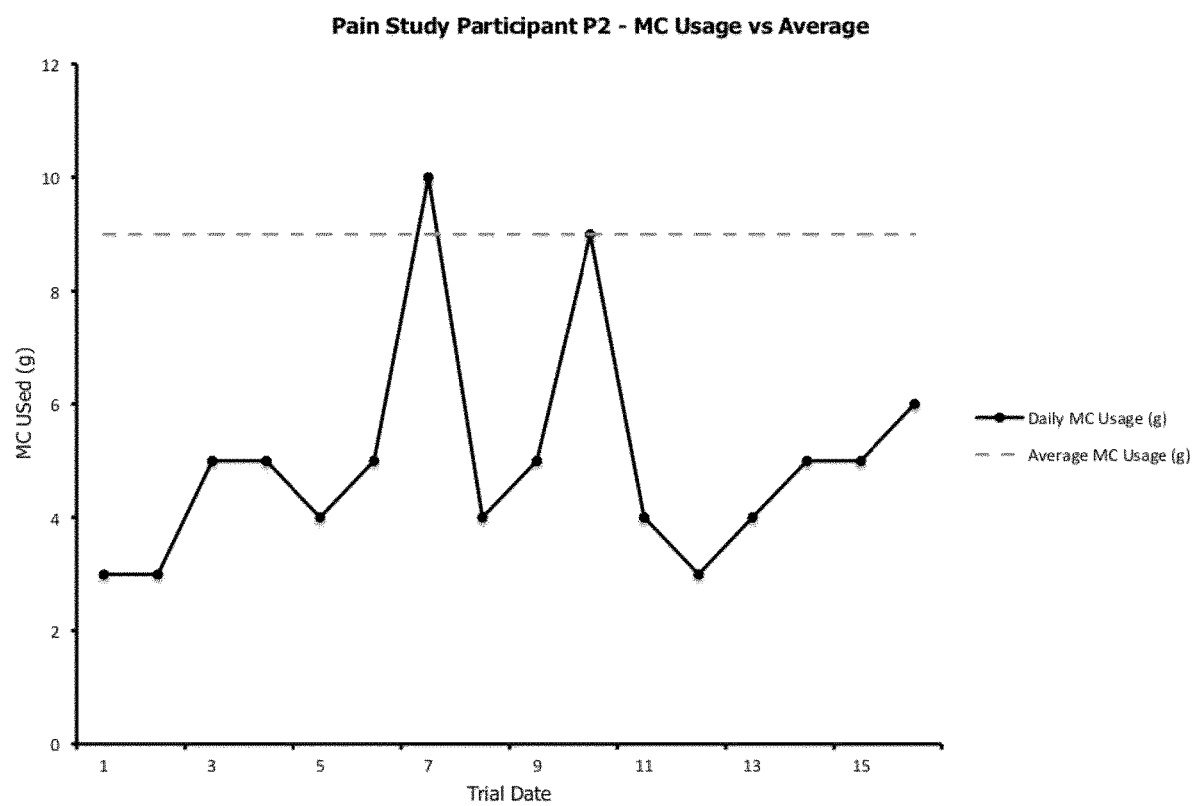
FIG. 12 shows a chart of smoked medical cannabis usage for patient P2, being treated with the composition described herein.
Figure 13:
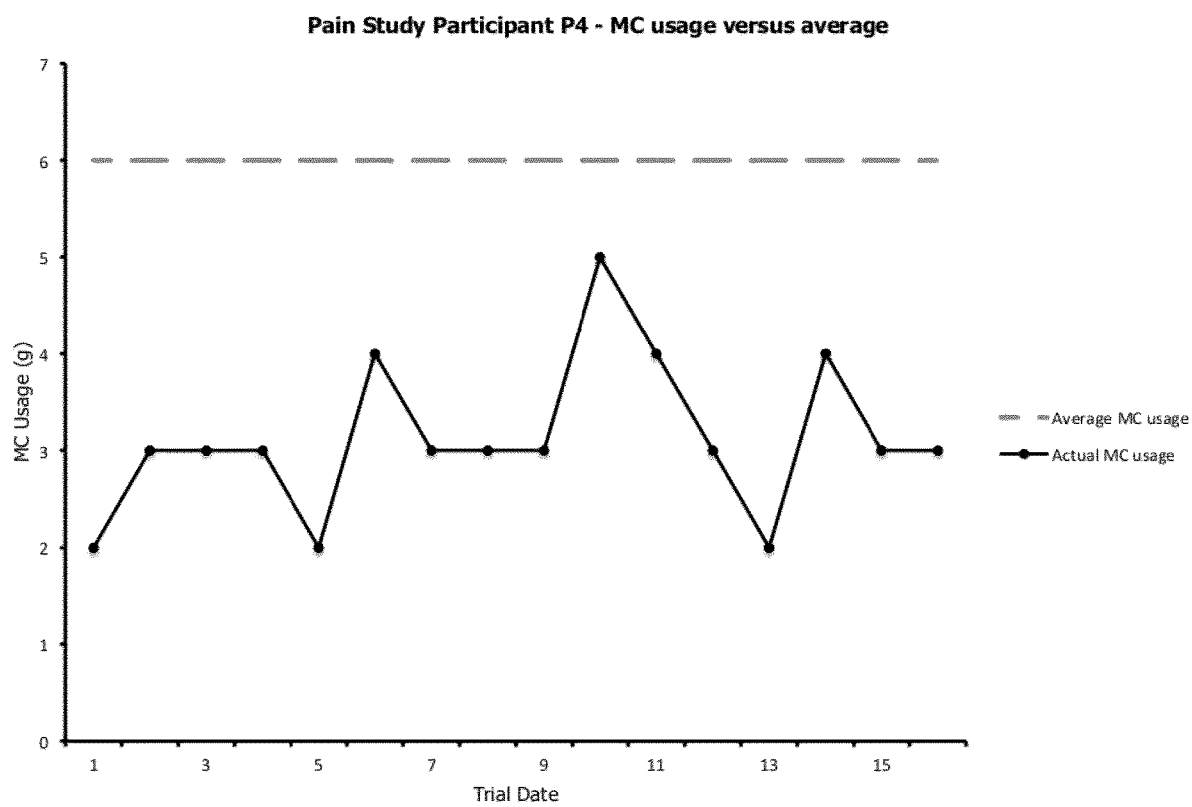
FIG. 13 shows a chart smoked medical cannabis usage for patient P4, being treated with the composition described herein.

Three persons noted non-trivial decreases in their consumption of smoked cannabis while involved in a case studies of the composition of Example 1: one patient from the arthritis study of Example 5, patient A4, and two patients from the study of Example 7, patients P2 and P4. Patients were asked to provide daily feedback, throughout the study, of how much cannabis they smoked, in any form, during the study. For these three patients, these self-reported amounts of smoked cannabis behaviour are displayed by the solid lines in FIGS. 9, 12, and 13, respectively. In FIGS. 12 and 13, each patient's average usage, evaluated by the patient prior to beginning to take the composition, is indicated by the dashed lines; this information was not supplied by the patient whose data are presented in FIG. 9. It is evident that, while using the composition these patients were able to get by with much less smoked cannabis than usual.

Example 9—Effectiveness in the Aftermath of Stroke

A 53 year old male who suffered from PTSD and depression noted during his participation in the study of Example 7 that he had suffered a stroke 18 months previously, and experienced numbness and loss of dexterity in his right hand and foot, and on the right side of his face. He observed "I'm noticing more feeling in my right foot and the numbness is fading," in the middle of the study, followed the next day by "these pills are great." He contributed similar comments related to his stroke on four additional days during the study.

A second participant in the study of Example 7 was a 39-year-old male who suffered a stroke 12 months prior to his participation in the study, and also complained of loss of feeling in his face and feet. On the 7th day of the trial he observed that he had "more feeling in my feet and less numbness in my face from the stroke I had last year." Other comments he provided throughout the trial included he was "feeling great," and, even more effusively, that, "after my first night I feel much better and happy to be alive," at one point also referring to the capsules as "life-saving."

Example 10—Effectiveness as a Sleep Aid

Two patients from the study of Example 7 noted improved sleep while participating. One, a 26-year-old female, suffered from Ehlers-Danlos Syndrome (type 3) and fibromyalgia. She experienced generalized pain, and complained of frequent waking at night due to pain flare-ups. On 10 out of the 14 times she commented during study she wrote statements like "no side effects save a good sleep!" and "almost sleeping through the night without waking up due to pain (woke up about 3 times.)" On the 14th day of the study she exclaimed "Deep sleep! No side effects!"

The other patient was a female in her early thirties who suffered from PTSD and depression, and complained of not sleeping well. However, in the first week of the study she wrote "I am in a bad cycle of not sleeping again and the capsules do a much better job of allowing me to sleep and stay asleep throughout the night." In a related vein, in the second week, she "noted a lot more of a physical relaxing and unexpected release of held tension."

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A tablet or capsule consisting essentially of an extract of flower bud tissue of sinsemilla cannabis, maltodextrin, hemp oil, and microcrystalline cellulose.

2. The tablet or capsule of claim 1, further consisting essentially of vitamin D.

3. A method of treating multiple sclerosis, muscle spasms, restless leg syndrome, stroke-related numbness, and/or a sleep apnea in a human in need thereof consisting essentially of administering the tablet or capsule of claim 1 to a human in need thereof to effectively treat the multiple sclerosis, muscle spasms, restless leg syndrome, stroke-related numbness, and/or a sleep apnea in said human in need thereof.

4. A method of reducing smoking cannabis in a human in need thereof consisting essentially of administering the tablet or capsule of claim 1 to said human in need thereof to effectively reduce the smoking of cannabis in the human in need thereof.

\* \* \* \* \*

UNITED STATES PATENT AND TRADEMARK OFFICE
CERTIFICATE OF CORRECTION

PATENT NO. : 10,765,713 B2
APPLICATION NO. : 16/311194
DATED : September 8, 2020
INVENTOR(S) : Walser et al.

Page 1 of 1

It is certified that error appears in the above-identified patent and that said Letters Patent is hereby corrected as shown below:

In the Specification

Column 16, Lines 52-53: Please correct "equivalent 20" to read -- equivalent $\leq$ 20 --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*